(12) United States Patent
Suzuki (10) Patent No.: US 10,493,236 B2
(45) Date of Patent: Dec. 3, 2019

(54) CATHETER

(71) Applicant: TERUMO KABUSHIKI KAISHA, Shibuya-ku, Tokyo (JP)

(72) Inventor: Kenta Suzuki, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 251 days.

(21) Appl. No.: 15/647,481

(22) Filed: Jul. 12, 2017

(65) Prior Publication Data

US 2017/0304591 A1   Oct. 26, 2017

Related U.S. Application Data

(63) Continuation of application No. PCT/JP2016/050299, filed on Jan. 7, 2016.

(30) Foreign Application Priority Data

Jan. 14, 2015  (JP) .................. 2015-005105

(51) Int. Cl.
*A61M 25/01* (2006.01)
*A61M 25/10* (2013.01)
(Continued)

(52) U.S. Cl.
CPC .......... *A61M 25/01* (2013.01); *A61M 25/008* (2013.01); *A61M 25/0009* (2013.01);
(Continued)

(58) Field of Classification Search
CPC ............. A61M 25/01; A61M 25/1036; A61M 25/0054; A61M 25/0014; A61M 25/0009;
(Continued)

(56) References Cited

U.S. PATENT DOCUMENTS 4,354,490 A * 10/1982 Rogers .................. A61M 39/16
604/256
5,762,637 A   6/1998 Berg et al.
(Continued)

FOREIGN PATENT DOCUMENTS

| JP | 9-192235 A | 7/1997 |
|----|------------|--------|
| JP | 2013-5976 A | 1/2013 |
| WO | WO 2013/140669 A1 | 9/2013 |

OTHER PUBLICATIONS

International Search Report (PCT/ISA/210) dated Mar. 8, 2016, by the Japanese Patent Office as the International Searching Authority for International Application No. PCT/JP2016/050299.

*Primary Examiner* — Julian W Woo
(74) *Attorney, Agent, or Firm* — Buchanan Ingersoll & Rooney PC (57) ABSTRACT

A catheter including a catheter shaft that has a proximal shaft and a distal shaft. The proximal shaft and the distal shaft are joined to one another in the axial direction. The proximal and distal shafts are integrally connected to one another by the distal end of the proximal shaft being inserted into a hollow interior of the proximal end of the distal shaft or by the proximal end of the distal shaft being inserted into a hollow interior of the distal end of the proximal shaft. The proximal shaft includes a penetrating portion which penetrates from the inner surface through to the outer surface at the distal end of the proximal shaft. The distal shaft includes a projecting portion that includes a tip portion which extends through the penetrating portion past the inner or outer surface of the proximal shaft so that the tip portion is exposed.

13 Claims, 8 Drawing Sheets

(51) Int. Cl.
*A61M 25/00* (2006.01)
*A61M 25/06* (2006.01)

(52) U.S. Cl.
CPC .... *A61M 25/0014* (2013.01); *A61M 25/0054* (2013.01); *A61M 25/0097* (2013.01); *A61M 25/0102* (2013.01); *A61M 25/0141* (2013.01); *A61M 25/10* (2013.01); *A61M 25/1034* (2013.01); *A61M 25/1036* (2013.01); *A61M 2025/0687* (2013.01)

(58) Field of Classification Search
CPC .......... A61M 25/0141; A61M 25/0102; A61M 25/0097; A61M 25/008; A61M 25/1034; A61M 25/10; A61M 2025/0687
USPC ................................................ 604/533–535
See application file for complete search history.

(56) References Cited

U.S. PATENT DOCUMENTS

| | | | | |
|---|---|---|---|---|
| 5,820,614 | A | * | 10/1998 | Erskine ............ A61M 5/16831 604/533 |
| 6,063,318 | A | * | 5/2000 | Houser ............ A61M 25/0012 156/304.2 |
| 6,066,114 | A | | 5/2000 | Goodin et al. |
| 6,500,285 | B2 | * | 12/2002 | Pepin ................ A61M 25/0009 156/158 |
| 6,921,397 | B2 | * | 7/2005 | Corcoran .......... A61M 25/0043 464/149 |
| 8,608,690 | B2 | * | 12/2013 | Pal .................... A61M 25/0009 604/103.04 |
| 10,315,018 | B2 | * | 6/2019 | Eidenschink ......... A61M 25/10 |
| 2014/0025045 | A1 | | 1/2014 | Abt et al. |
| 2015/0005803 | A1 | | 1/2015 | Erikawa |

* cited by examiner

CATHETER

CROSS-REFERENCES TO RELATED APPLICATIONS

This application is a continuation of International Application No. PCT/JP2016/050299 filed on Jan. 7, 2016, and claims priority to Japanese Patent Application No. 2015-005105 filed on Jan. 14, 2015, the entire content of both of which is incorporated herein by reference.

TECHNICAL FIELD

The present invention generally relates to a catheter having a catheter shaft that is formed by joining a plurality of shafts. More specifically, this application relates to the shaft of a catheter that possesses improved joining strength. The application also relates to a method of manufacturing the catheter.

BACKGROUND DISCUSSION

Treatment of vascular lesion using a catheter is widely performed because it introduces less surgical stress in a living body. For example, a balloon catheter is used for dilating a lesion area in a coronary artery and improving a blood flow in Percutaneous Transluminal Coronary Angioplasty (PTCA). The balloon catheter generally includes an elongated hollow catheter shaft, a balloon provided on a distal side of the catheter shaft, and a hub provided on a proximal side of the catheter shaft.

The catheter shaft is required to have a pushing performance which contributes to reliably transmit a pushing force of an operator from a proximal side to a distal side of the catheter because the catheter may be inserted into blood vessels having complicated curves. The catheter shaft also needs to have a followability (i.e., maneuverability) which helps to smoothly and reliably advance the catheter in a blood vessel in a living body along a leading guide wire. Catheters are known to be configured to achieve both of these properties by making a proximal side of a catheter shaft of a material having a high flexural stiffness and a distal side of the catheter shaft of a material having less flexural stiffness than the proximal side and being relatively highly flexible (i.e., possess relatively high flexibility), and joining both sides together in an axial direction. For example, Japanese Patent Application No. 2013-005976 discloses a catheter with a catheter shaft having a high flexural stiffness joined to a distal catheter shaft having less flexural stiffness.

SUMMARY

The joint structure between the shaft on the distal side and the shaft on the proximal side is generally achieved by forming one of the shafts to have an outer diameter which allows insertion into a hollow interior of the other shaft. The joining of the two shafts is then accomplished by inserting an end portion of the one shaft into the hollow interior of the other shaft, and fixing both of the shafts to one another by crimping, adhesion, or a combination of crimping and adhesion.

A fluid such as an X-ray contrast agent may be injected into the catheter shaft to inflate a balloon provided at a distal portion. The catheter shaft thus becomes pressurized from inside. The joint portion of the shaft may thus be subjected to a force in a direction in which the shafts separate from each other when the fluid is injected into the catheter shaft. Therefore, the joint portion of the shaft has a risk of separation or disconnection of the shafts due to this separation. Joining by means of crimping or adhesion may not ensure a joining strength sufficient for resisting the force of separation of the shafts.

The catheter disclosed in this application has a catheter shaft that includes a shaft on the proximal side and a shaft on the distal side integrated with one another with a high joining strength.

A catheter disclosed in this application more specifically may include a catheter shaft that has a proximal shaft and a distal shaft. The proximal shaft and the distal shaft are joined to one another in the axial direction. The proximal and distal shafts are integrally connected to one another by the distal end of the proximal shaft being inserted into a hollow interior of the proximal end of the distal shaft or by the proximal end of the distal shaft being inserted into a hollow interior of the distal end of the proximal shaft. The proximal shaft includes a penetrating portion which penetrates from the inner surface through to the outer surface at the distal end of the proximal shaft. The distal shaft includes a projecting portion that includes a tip portion which extends through the penetrating portion past the inner or outer surface of the proximal shaft so that the tip portion is exposed.

In another aspect, the catheter includes a catheter shaft extending in an axial direction from a proximal end to a distal end. The catheter shaft includes a proximal shaft and a distal shaft that are each a hollow cylinder. The proximal end of the distal shaft is proximal to the distal end of the proximal shaft so that the distal and proximal shafts overlap in the axial direction along a joint. The proximal shaft and the distal shaft are integrally connected to one another at the joint by the distal end of the proximal shaft being inserted into a hollow interior of the proximal end of the distal shaft. The proximal shaft includes a penetrating portion which penetrates from the inner surface through to the outer surface at the distal end of the proximal shaft. The distal shaft includes a projecting portion that extends radially inward from the inner surface of the distal shaft. The projecting portion extends through the penetrating portion of the proximal shaft to the inner surface of the proximal shaft. The projecting portion includes a tip portion which extends radially inwardly beyond the inner surface of the proximal shaft.

In the catheter described above, the distal shaft includes the projecting portion configured to penetrate from the one surface to the other surface of the proximal shaft through the penetrating portion of the proximal shaft. The tip portion of the projecting portion is exposed from the inner surface or the outer surface of the penetrating portion. The projecting portion of the distal shaft thus enters the joint portion from an inner surface side to an outer surface side of the proximal shaft or enters the joint portion from the outer surface side to the inner surface side of the proximal shaft, so that a high joining strength between the distal and proximal shafts is achieved. The catheter shaft may accordingly help prevent separation of the joint surfaces of the proximal shaft and the distal shaft from each other to help prevent the proximal shaft and the distal shaft from disconnecting.

With a distal end portion of the proximal shaft inserted into a hollow interior of a proximal end portion of the distal shaft, the projecting portion of the distal shaft penetrates from the outer surface side to the inner surface side of the proximal shaft through the penetrating portion to be exposed at the inner surface of the proximal shaft. The projecting portion may be formed while crimping the proximal shaft and the distal shaft easily by applying heat and pressure from outside the distal shaft (e.g., using a shrinkable tube that covers the outer surface of the proximal end portion of the distal shaft).

The projecting portion may have a structure that does not come out easily (i.e., separate relatively easily) from the penetrating portion because the tip portion of the projecting portion (exposed at the inner surface of the proximal shaft) is provided with an enlarged portion having a width larger than the penetrating portion (e.g., the inner diameter of the penetrating portion). Therefore, separation of the joint surfaces of the proximal shaft and the distal shaft from each other and disconnection between the proximal shaft and the distal shaft may be prevented further reliably.

The penetrating portion may be formed easily on the proximal shaft by forming the penetrating portion as a hole or a slit through a peripheral surface of the proximal shaft.

With the proximal shaft made of a metallic material and the distal shaft made of a resin material, an effect of fixation between the proximal and distal shafts with the projecting portion at a joint between the metallic material and the resin material by crimping is further improved. More specifically, improvement of the joining strength at joining surfaces of the metallic material and the resin material is difficult because the metallic material and the resin material do not fuse together. However, with the catheter shaft disclosed in this application, a physical joint structure at the joining surfaces of the proximal shaft and the distal shaft is achieved by using the projecting portion. The joining strength at the joining surfaces may thus be improved.

The distal shaft may be provided with a balloon on the outer surface of the distal shaft at the distal end side (i.e., distal to the projecting portion). An interior of the catheter shaft of the catheter is pressurized when the balloon is inflated. The joining surfaces of the proximal shaft and the distal shaft are susceptible to separation or the proximal shaft and the distal shaft are susceptible to disconnection due to the pressure in the interior of the catheter shaft. However, such separation and disconnection may reliably be prevented by joining the proximal and distal shafts as described above.

With the additional provision of a reinforcement body extending distally from the distal end portion of the proximal shaft and disposing a proximal end portion of the reinforcement body distal to one or ones of the penetrating portions of the proximal shaft located at the distal-most position, the reinforcement body may be extended linearly from the end portion of the proximal shaft toward the distal shaft without interference of the reinforcement body with the projecting portion. Therefore, bending properties of the catheter shaft may not be adversely affected. When joining the proximal shaft and the distal shaft, a core bar member may additionally be prevented from interfering with the reinforcement body, so that the reinforcement body is not deformed.

This application also relates to a catheter shaft manufacturing method that includes inserting the end portion of a first catheter shaft into the end portion of a second catheter shaft. The first and second catheter shafts are hollow cylinders that each possess an interior. The inner diameter of the second catheter shaft is substantially equal to the outer diameter of the first catheter shaft so that the inner surface of the second catheter shaft is located immediately adjacent to the outer surface of the first catheter shaft. The end portion of the first catheter shaft includes a penetrating portion. The method further includes positioning a core bar within the interior of the first catheter shaft. The core bar possesses an outer diameter that is less than the inner diameter of the first catheter shaft so that a gap is between an outer surface of the core bar and the inner surface of the first catheter shaft. The method includes covering the outer surface of the end portion of the second catheter shaft with a shrinkable tube while the end portion of the first catheter shaft is within the end portion of the second catheter shaft and while the core bar is within the interior of the first catheter shaft, and heating the shrinkable tube to shrink the inner diameter of the shrinkable tube so that the shrinkable tube compresses the end portion of the second catheter shaft radially inward. The heating also softens a material of the second catheter shaft so that a portion of the material of the second catheter flows radially inward through the penetrating portion of the first catheter shaft. The method includes cooling the first catheter shaft and the second catheter shaft so that a catheter shaft is formed with the first and second catheter shafts joined together.

DETAILED DESCRIPTION

Set forth below with reference to the accompanying drawings is a detailed description of embodiments of a catheter and method of manufacturing a catheter representing examples of the inventive catheter and method disclosed here. Note that dimensional ratios of the drawings may be exaggerated and thus may be different from actual ratios for the sake of convenience of description. In this specification, the side of a catheter 10 which is to be inserted towards or into a body lumen in a living body is referred to as the "distal", "distal end" or "distal side", and a near side to be operated by an operator outside of the living body is referred to as "proximal", "proximal end" or "proximal side".

Figure 1:
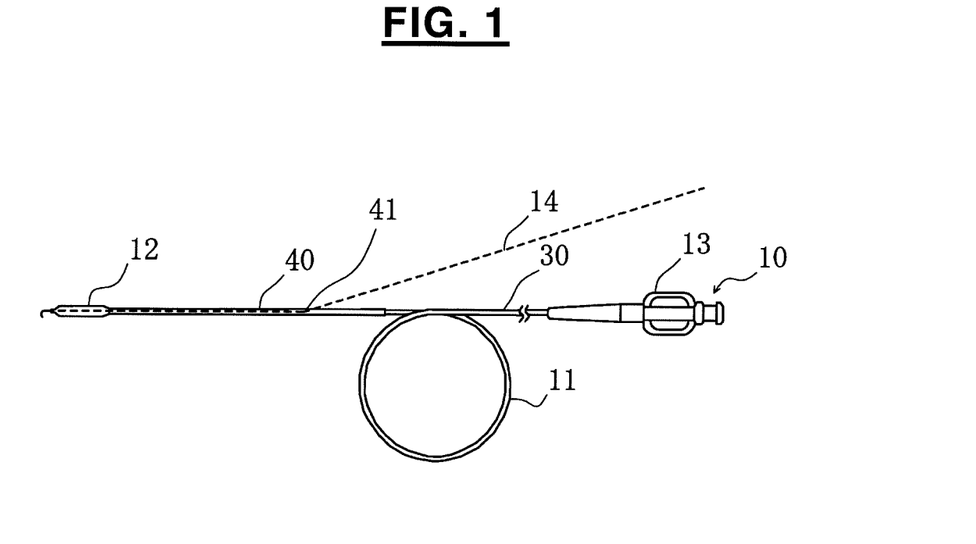
FIG. 1 is a drawing illustrating a general configuration of one embodiment of a catheter.

The configuration of a catheter 10 will first be described. The catheter 10 includes an elongated hollow catheter shaft 11, a balloon 12 provided at a distal end portion of the catheter shaft 11, and a hub 13 secured to a proximal end portion of the catheter shaft 11 as illustrated in FIG. 1.

The catheter 10 is capable of dilating (expanding or widening) a lesion area for treatment by inserting the elongated catheter shaft 11 into a biological organ and inflating the balloon 12 provided on the distal side of the catheter shaft 11 while the balloon 12 is in the lesion area.

The catheter shaft 11 is provided with an opening portion 41 for introducing a guide wire 14 (i.e., configured so that a guide wire 14 can be inserted through the opening portion 41) at a position biased toward the distal side of the catheter shaft 11. In other words, the catheter 10 of the embodiment illustrated in FIG. 1 is a so-called rapid exchange type catheter. The catheter shaft 11 includes a proximal shaft 30 on the proximal side and a distal shaft 40 on the distal side joined to one another in an axial direction and integrated (i.e., integrally joined in an axially overlapping manner or interconnected).

Figure 2:
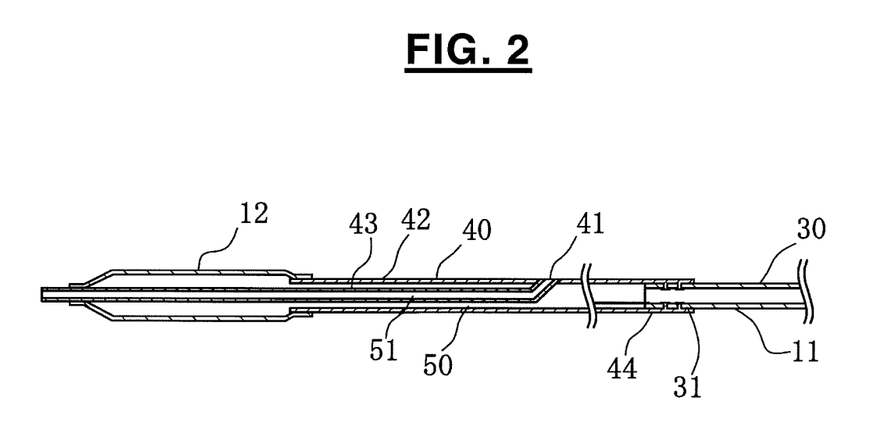
FIG. 2 is a cross-sectional view of a catheter shaft and a balloon.

The proximal shaft 30 and the distal shaft 40 are joined in the axial direction at an intermediate position of the catheter shaft 11 as illustrated in FIG. 2. The distal shaft 40 has an inner diameter slightly larger than the outer diameter of the proximal shaft 30. An end portion 31 (i.e., a distal end) of the proximal shaft 30 is inserted into an end portion 44 (i.e., a proximal end) of the distal shaft 40, and both shafts are joined together.

The distal side of the catheter shaft 11 with respect to the opening portion 41 (i.e., the portion of the catheter shaft 11 that is distal to the opening portion 41) has a double tube structure. The double tube structure includes an outer tube 42 and an inner tube 43 arranged in a concentric manner. The outer tube 42 extends distally to a proximal end portion of the balloon 12 (i.e., the distal end of the outer tube 42 is at the proximal end portion of the balloon 12) and is provided with an inflation lumen 50 in an interior of the outer tube 42. Fluid for inflating the balloon 12 may be injected into the inflation lumen 50. The proximal side of the catheter shaft 11 with respect to the opening portion 41 (i.e., the portion of the catheter shaft 11 that is proximal to the opening portion 41) has a single tube structure, and the interior thereof continues from the inflation lumen 50 in the outer tube 42.

The distal end of the inner tube 43 extends distally beyond the distal end portion of the balloon 12. The distal end of the inner tube 43 is provided with a guide wire lumen 51 in which the guide wire 14 is configured to be inserted in an interior of the guide wire lumen 51.

The distal side of the balloon 12 is adhered to the inner tube 43, and the proximal side is adhered to the outer tube 42. An interior of the balloon 12 is in communication with the inflation lumen 50. The balloon 12 may thus be inflated by injection of the inflation fluid through the inflation lumen 50. The injection fluid can be gas or liquid. For example, gas such as helium gas, $CO_2$ (carbon dioxide) gas, $O_2$ (oxygen) gas, and liquid such as physiological salt solution and contrast agent may be used.

The proximal shaft 30 in the embodiment of the catheter illustrated in FIG. 1 is made of a metallic material such as stainless steel and aluminum. The distal shaft 40 in the embodiment of the catheter illustrated in FIG. 1 is made of a resin material having a thermoplastic property. Specific examples of the distal shaft 40 material include polyolefin such as polyethylene, polypropylene, polybutene, ethylene-propylene copolymer, ethylene-vinyl acetate copolymer, ionomer, and mixture of two or more of these components, soft polyvinyl chloride resin, polyamide, polyamide elastomer, polyester, polyester elastomer, polyurethane, and fluorine resin such as polytetrafluoroethylene.

Improvement of pushing performance of the catheter 11 is achieved because the proximal shaft 30 is made of a metallic material. Improvement of followability that ensures smooth and reliable advance in a blood vessel is achieved because the distal shaft 40 is made of a resin material. The disclosed catheter possesses a structure in which the proximal shaft 30 made of a metallic material and the distal shaft 40 made of a resin material are joined with a high strength. This point will be described below.

Figure 3:
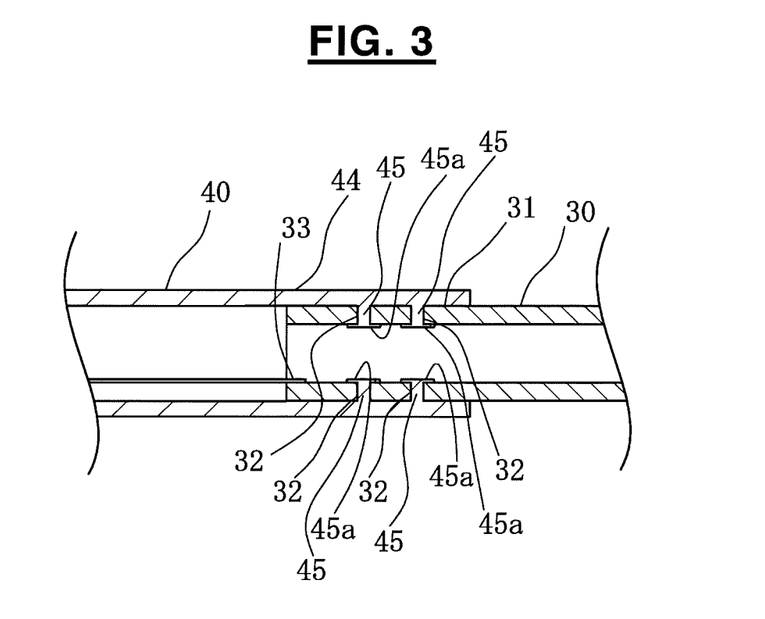
FIG. 3 is an enlarged cross-sectional view of a portion near a joint portion of the catheter shaft.
Figure 4:
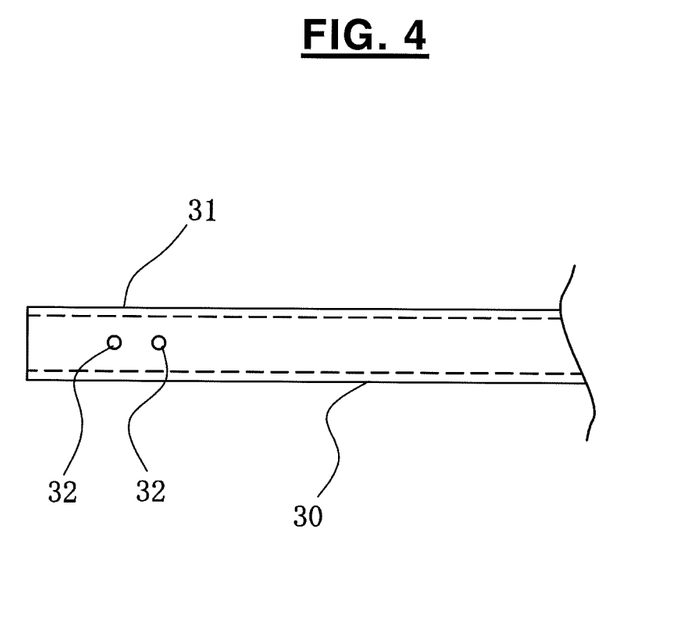
FIG. 4 is a plan view near an end portion of a proximal shaft.

As illustrated in FIGS. 3 and 4, the end portion 31 (distal end) of the proximal shaft 30 that is inserted into the end portion 44 (proximal end) of the distal shaft 40 is provided with penetrating portions 32 that penetrate therethrough between the inner surface and the outer surface of the proximal shaft 30 (i.e., the penetrating portions 32 are through-holes that penetrate fully from the inner surface to the outer surface of the proximal shaft 30). The penetrating portions 32 are each formed of a circular through hole as illustrated in FIG. 4. A plurality of the penetrating portions 32 are formed in a circumferential direction and an axial direction of the proximal shaft 30, respectively. In the embodiment illustrated in FIGS. 3 and 4, four penetrations 32 are included. Two of the penetrating portions 32 are spaced apart from the other two penetrating portions 32 in the axial direction, and two of the penetrating portions are spaced apart from the other two penetrating portions 32 at positions 180 degrees away from each other in the circumferential direction.

The number and the positions of the penetrating portions 32 are not limited to four penetrating portions or to the illustrated positions. The number and positions of the penetrating portions 32 may be selected as needed depending on the required joining strength. The shape of the hole of the penetrating portions 32 is not limited to being circular, but may be other shapes such as a square shape and an oval shape.

The end portion 31 of the proximal shaft 30 and the end portion 44 of the distal shaft 40 are joined together by crimping. As illustrated in FIG. 3, an internal surface of the end portion 44 of the distal shaft 40 is provided with projecting portions 45 that penetrate through the penetrating portions 32 of the proximal shaft 30 from an outer surface side to an inner surface side (i.e., radially inward). Tip portions of the projecting portions 45 are exposed from the inner surface side of the proximal shaft 30, and each of the tip portions include an enlarged portion 45a larger in width (i.e., wider) than the width of each of the penetrating portions 32. In other words, the inner surface side of the distal shaft 40 made of a resin material has a shape that enters the hollow interior of the proximal shaft 30 through the penetrating portions 32 and cannot be disconnected from the penetrating portions 32. As used herein the expression "the tip portions of the projecting portions 45 are exposed from the inner surface side of the proximal shaft 30" is intended to mean that the tip portions of the projecting portions 45 protrude to a level flush with or inner than (i.e., more radially inward than) the inner surface of the proximal shaft 30. In other words, the tip portions of the projecting portions 45 protrude without staying entirely in the interior of the penetrating portions 32.

In this manner, the joining strength between the proximal shaft 30 and the distal shaft 40 is improved by configuring the proximal shaft 30 with the penetrating portions 32 and the distal shaft 40 with the projecting portions 45 that enter the hollow interior of the proximal shaft 30 through the penetrating portions 32. When the interior of the catheter shaft 11 is pressurized in order to inflate the balloon 12, separation of the joint portion of the proximal shaft 30 and the distal shaft 40 from each other or disconnection between the proximal shaft 30 and the distal shaft 40 may be prevented.

As the proximal shaft 30 is made of a metallic material and the distal shaft 40 is made of a resin material, the joining strength between the proximal shaft 30 and the distal shaft 40 if joint is made by crimping is lower than when forming a joint between resins by crimping. However, sufficient joining strength may be ensured by the projecting portions 45 entering the hollow interior of the proximal shaft 30 in addition to joining by crimping.

The distal end portion of the proximal shaft 30 is provided with a metallic reinforcement body 33. The reinforcement body 33 is an elongated wire member that is joined to the hollow interior of the proximal shaft 30 by welding. The reinforcement body 33 is not limited to a solid wire member. The reinforcement body 33 may be other shapes such as a half pipe shaped elongated member. The proximal shaft 30 made of a metallic material and the distal shaft 40 made of a resin material are significantly different in flexural rigidity. Therefore, the joint portion between the proximal shaft 30 and the distal shaft 40 is susceptible to collapse and kink of the distal shaft 40. An abrupt change in flexural rigidity can be alleviated, and collapse and kink of the distal shaft 40 can be prevented, however by including the metallic reinforcement body 33 extending from the end portion of the proximal shaft 30 toward the distal shaft 40.

A proximal end portion of the reinforcement body 33 is distal to the penetrating portion 32 or penetrating portions 32 of the proximal shaft 30 that are disposed at a distal-most position (i.e., the reinforcement body 33 is entirely distal to the distal-most penetrating portion(s) 32). Accordingly, a core bar member 60 (described below) may be prevented from interfering with the reinforcement body 33, and thus deformation or the like of the reinforcement body 33 may be prevented when forming the projecting portions 45. The bending properties (i.e., bendability or flexibility) of the catheter shaft 11 are not adversely affected because the reinforcement body 33 is restricted from interfering with the projecting portions 45 made of a resin material, and the reinforcement body 33 may be extended linearly from the distal end portion of the proximal shaft 30 toward the distal shaft 40. The proximal end portion of the reinforcement body 33 may be distal to the projecting portion 45 or projecting portion 45 of the distal shaft 40 disposed at the distal-most position (i.e., the distal-most projecting portion(s) 45. The reinforcement body 33 may accordingly be further prevented from interfering with the projecting portions 45 made of a resin material.

A joint process for joining the proximal shaft 30 and the distal shaft 40 to one another is next described. Prior to the joint process, the proximal shaft 30 made of a metal and having predetermined diameter and length, and the distal shaft 40 made of a resin and having predetermined diameter and length, are fabricated in advance. The penetrating portions 32 are provided in the proximal shaft 30 in advance, and the reinforcement body 33 is joined to the distal end portion of the proximal shaft 30 by welding.

Figure 5:
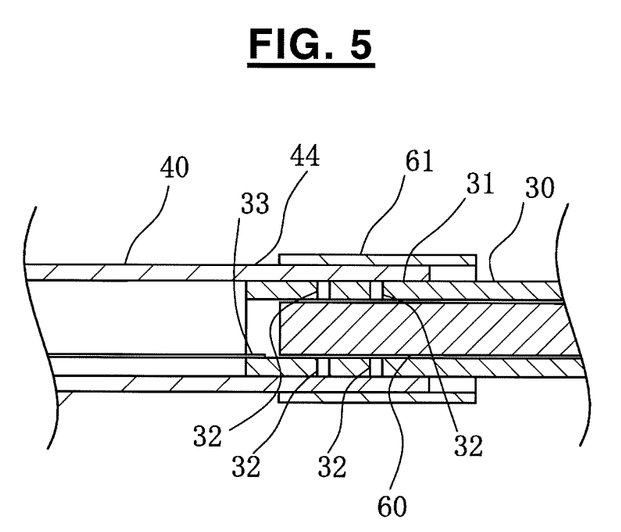
FIG. 5 is an enlarged cross-sectional view illustrating a portion near the joint portion in a stage in which the joint portion is covered with a shrinkable tube in a joint process for joining the proximal shaft and a distal shaft.

In the joint process, the distal end portion 31 of the proximal shaft 30 is first inserted into the proximal end portion 44 of the distal shaft 40 as illustrated in FIG. 5. The proximal shaft 30 is inserted into the distal shaft 40 so that all of the penetrating portions 32 stay in the hollow interior of the distal shaft 40. The outer diameter of the proximal shaft 30 is formed to be equivalent to the inner diameter of the distal shaft 40, so that the outer surface of the proximal shaft 30 is brought into substantially tight contact with the inner surface of the distal shaft 40. In other words, the outer diameter of the proximal shaft 30 is substantially equal to (e.g., slightly greater than) the inner diameter of the distal shaft 40 so that the outer surface of the proximal shaft is immediately adjacent (i.e., opposite) the inner surface of the distal shaft.

The core bar member 60 is inserted into the hollow interior of the proximal shaft 30. The core bar member 60 is a metallic rod member and possesses an outer diameter that is slightly smaller than the inner diameter of the proximal shaft 30. Therefore, a minute (relatively small) gap is formed between the core bar member 60 and the inner surface of the proximal shaft 30. The distal end of the core bar member 60 is positioned distal to the distal-most of the penetrating portions 32 of the proximal shaft 30 and proximal to the proximal end portion of the reinforcement body 33.

A portion where the proximal shaft 30 and the distal shaft 40 overlap with each other is covered with a shrinkable tube 61 that shrinks by being heated. The shrinkable tube 61 is made of a material such as polyolefin, which shrinks in diameter after being heated (i.e., the inner diameter of the shrinkable tube 61 after being heated is smaller than the inner diameter of the shrinkable tube 61 before being heated). The shrinkable tube 61 thus contributes to pressurize the distal shaft 40 radially inward from outside of the distal shaft 40 by being heated. In contrast, the end portion 31 of the proximal shaft 30 and the end portion 44 of the distal shaft 40 that overlap with each other are compressed in the thickness direction of the catheter shaft 11 because the core bar member 60 is disposed in the hollow interior of the proximal shaft 30, so that the end portion 31 of the proximal shaft 30 and the end portion 44 of the distal shaft 40 are interposed between the shrinkable tube 61 and the core bar member 60.

Figure 6:
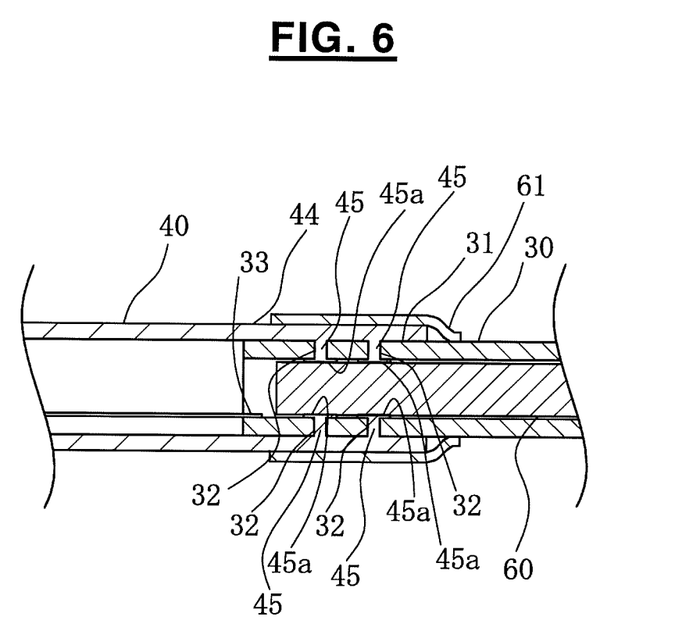
FIG. 6 is an enlarged cross-sectional view illustrating a portion near the joint portion in a stage in which the shrinkable tube shrinks in the joint process for joining the proximal shaft and the distal shaft.

The joint portion between the proximal shaft 30 and the distal shaft 40 is heated to a temperature at which the resin material forming the distal shaft 40 softens. As described above, the end portion 44 of the distal shaft 40 is crimped to the end portion 31 of the proximal shaft 30 since the distal shaft 40 and the proximal shaft 30 are pressurized in the direction of compression with the shrinkable tube 61 that shrinks by being heated. At this time, the softened resin material of the distal shaft 40 enters the interior of the penetrating portions 32 of the proximal shaft 30, penetrates through the penetrating portions 32, and enters the hollow interior of the proximal shaft 30. The resin material of the distal shaft 40 entering the hollow interior of the proximal shaft 30 spreads in a space between the proximal shaft 30 and the core bar member 60 and forms an enlarged portion having a wider width than the penetrating portions 32. The projecting portions 45 having the enlarged portions 45a are thereby formed.

The proximal shaft 30 and the distal shaft 40 are crimped together and the projecting portions 45 are formed, so that both shafts are joined with a high strength (i.e., a relatively high joining force is created between the proximal and distal shafts 40). After being heated, the catheter shaft 11 is cooled to a room temperature, the core bar member 60 is pulled out from the proximal shaft 30, and the shrinkable tube 61 is separated from the joint portion between the proximal shaft 30 and the distal shaft 40. The joint forming process is thus completed.

Figure 7:
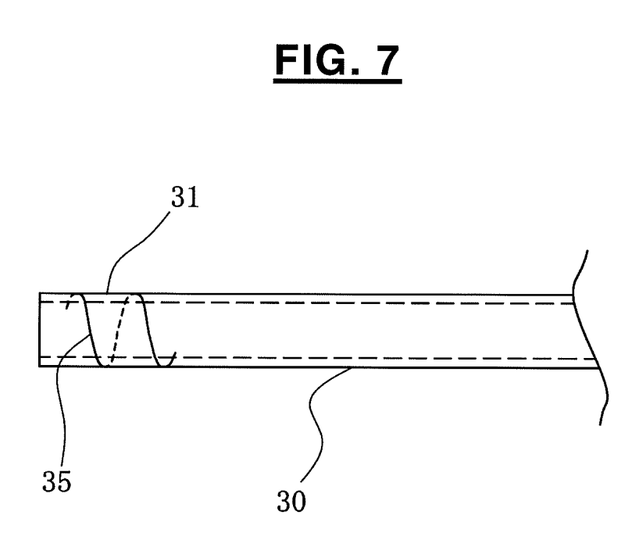
FIG. 7 is a plan view near the end portion of the proximal shaft having penetrating portions of another mode.

Another embodiment of the penetrating portion is next described. As illustrated in FIG. 7, a penetrating portion 35 of this embodiment is formed by a series of slit cut into a peripheral surface of the proximal shaft 30 in a helical shape. The proximal shaft 30 is resiliently deformed in such a manner that the helical slit opens as the proximal shaft 30 is compressed in the circumferential direction.

The proximal shaft 30 having the penetrating portion 35 of this embodiment may be joined with the distal shaft 40 in the same process as the proximal shaft 30 having the hole-type penetrating portions 32. In other words, the end portion 31 (distal end) of the proximal shaft 30 is inserted into the end portion 44 (proximal end) of the distal shaft 40, the core bar member 60 is inserted into the hollow interior of the proximal shaft 30, and the joint portion is covered with the shrinkable tube 61 from the outside of the distal shaft 40. By heating the joint portion, the distal shaft 40 softens, and the shrinkable tube 61 is shrunk and compressed onto the outer surface of the distal shaft 40, so that the resin material of the distal shaft 40 is crimped to the proximal shaft 30, and so that the resin material of the distal shaft 40 enters the hollow interior of the proximal shaft 30 through the slit of the penetrating portion 35, which is opened by being compressed.

Figure 8:
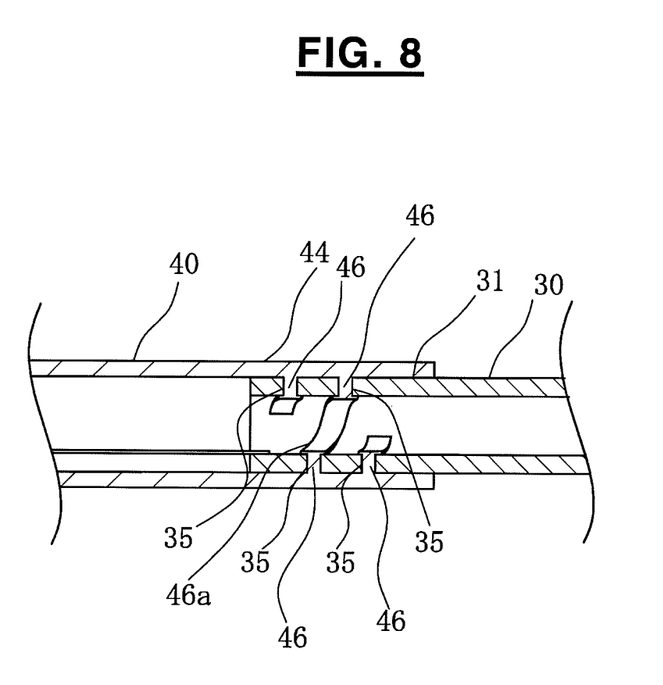
FIG. 8 is a cross-sectional view illustrating a portion near the joint portion between the proximal shaft having penetrating portions of another mode and the distal shaft.

As illustrated in FIG. 8, the resin material of the distal shaft 40 entering the hollow interior of the proximal shaft 30 through the penetrating portions 35 forms projecting portions 46 penetrating through the penetrating portions 35. The projecting portions 46 possess tip portions which are enlarged portions 46a having a larger width than the penetrating portions 35. The projecting portion 46 has a shape continuing in the circumferential direction of the proximal shaft 30 in the embodiment illustrated in FIG. 8.

As described above, the catheter shaft 11 of the catheter 10 of this application is configured in such a manner that the proximal shaft 30 on the proximal side formed into a hollow shape and the distal shaft 40 on the distal side formed into a hollow shape are joined in the axial direction. The proximal shaft 30 and the distal shaft 40 are integrated (i.e., integrally joined in an axially overlapping manner or interconnected) by an end portion of one of the proximal shaft 30 and the distal shaft 40 inserted into a hollow interior of an end portion of the other of the proximal shaft 30 and the distal shaft 40. The proximal shaft 30 may include the penetrating portion 32 which penetrates through the proximal shaft 30 in the thickness direction between the inner surface and the outer surface at the end portion of the proximal shaft. The distal shaft 40 may include a projecting portion 45 that penetrates from one surface toward the other surface of the proximal shaft through the penetrating portion 32. A tip portion of the projecting portion 45 exposes from the inner surface or the outer surface of the proximal shaft through the penetrating portion 32 (i.e., penetrates fully through the penetrating portion 32 to be exposed on the inner surface or the outer surface of the proximal shaft). Therefore, the projecting portions 45 of the distal shaft 40 enter from one surface to the other surface of the proximal shaft 30 at the joint portion between the proximal shaft 30 and the distal shaft 40, so that separation of joint surfaces of the proximal shaft 30 and the distal shaft 40 from each other may be prevented, and a high joining strength between the proximal shaft 30 and the distal shaft 40 is achieved. Accordingly, the catheter shaft 11 of the catheter 10 of the embodiment illustrated in FIG. 3 may prevent separation of the joint surfaces of the proximal shaft 30 and the proximal shaft 40 from each other and disconnection between the proximal shaft 30 and the distal shaft 40.

The distal end portion of the proximal shaft 30 is inserted into the hollow interior of the end portion of the distal shaft 40, and the projecting portions 45 of the distal shaft 40 penetrate from the outer surface side to the inner surface side of the proximal shaft 30 (i.e., radially inward) through the penetrating portions 32 to be exposed at the inner surface of the proximal shaft 30. Therefore, the projecting portions 45 may be formed while crimping the proximal shaft 30 and the distal shaft 40 easily by heating and pressing from outside of the distal shaft 40.

The tip portions of the projecting portions 45 exposing from the inner surface of the proximal shaft 30 have the enlarged portion 45a having a width larger than the penetrating portions 32. Therefore, a structure in which the projection portions 45 cannot come apart easily from the penetrating portions 32 is achieved and separation of the joint surfaces of the proximal shaft 30 and the distal shaft 40 from each other and disconnection between the proximal shaft 30 and the distal shaft 40 may be prevented further reliably.

The penetrating portions 32 are holes or a slit 35 formed on the peripheral surface of the proximal shaft 30. Therefore, the penetrating portions 32 may be easily formed in the proximal shaft 30.

The proximal shaft 30 is made of a metallic material, and the distal shaft 40 is made of a resin material. The fixation between the proximal shaft 30 and the distal shaft 40 with the projecting portion 45 at a joint between the metallic material and the resin material by crimping may thus be further improved.

The distal shaft 40 may include the balloon 12 on the distal side of the distal shaft 40. In this case, the interior of the catheter shaft 11 of the catheter 10 is pressurized when the balloon 12 is inflated. The joining surfaces of the proximal shaft 30 and the distal shaft 40 are susceptible to separation or the proximal shaft 30 and the distal shaft 40 are susceptible to disconnection due to the pressure in the interior of the catheter shaft 11. However, such separation and disconnection may reliably be prevented as discussed above.

The reinforcement body 33 extending distally from the distal end portion of the proximal shaft 30 is also provided, and the proximal end portion of the reinforcement body 33 is disposed distal to the penetrating portions 32 or penetrating portion 32 of the proximal shaft 30 disposed at the distal-most position. Therefore, the reinforcement body 33 is prevented from interfering with the projecting portions 45, and the reinforcement body 33 may be extended linearly from the end portion of the proximal shaft 30 toward the distal shaft 40. Bending properties of the catheter shaft 11 are thus not adversely affected. When joining the proximal shaft 30 and the distal shaft 40, the core bar member 60 may be prevented from interfering with the reinforcement body 33, so that the reinforcement body 33 may be prevented from being deformed.

Note that the catheter of this application is not limited only to the embodiments described above, and various modifications may be made by one of ordinary skill in the art within a technical scope of the disclosed catheter. For example, in the embodiment described above, the catheter has the balloon 12. However, configurations that do not have a balloon are also applicable, and configurations on which a stent is mounted on the balloon are also applicable.

In the above-described embodiments, the proximal shaft 30 made of a metallic material and the distal shaft 40 made of a resin material are joined to one another. However, the distal shaft 40 may further include a plurality of shafts. The proximal shaft 30 may be made of a resin material.

The detailed description above describes a catheter and method of manufacturing a catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
a catheter shaft extending in an axial direction from a proximal end to a distal end, the catheter shaft possessing a proximal side and a distal side;
the catheter shaft comprising a proximal shaft formed into a hollow shape and provided on the proximal side and a distal shaft formed into a hollow shape and provided on the distal side of the catheter shaft, the proximal shaft possessing a distal end, a proximal end, an inner surface and an outer surface, the distal shaft possessing a proximal end, a distal end, an inner surface and an outer surface, the proximal shaft and the distal shaft being joined to one another in the axial direction;
the proximal shaft and the distal shaft being integrally connected to one another by the distal end of the proximal shaft being inserted into a hollow interior of the proximal end of the distal shaft or by the proximal end of the distal shaft being inserted into a hollow interior of the distal end of the proximal shaft;
the proximal shaft comprising a penetrating portion which penetrates from the inner surface through to the outer surface at the distal end of the proximal shaft;
the distal shaft includes a projecting portion that penetrates from the outer surface toward the inner surface of the proximal shaft through the penetrating portion or penetrates from the inner surface toward the outer surface of the proximal shaft through the penetrating portion when the proximal end of the distal shaft is inserted into the hollow interior of the distal end of the proximal shaft; and
the projecting portion comprises a tip portion which extends through the penetrating portion past the inner surface or past the outer surface of the proximal shaft so that the tip portion is exposed.

2. The catheter according to claim 1, wherein the distal end of the proximal shaft is inserted into the hollow interior of the proximal end of the distal shaft, and the projecting portion of the distal shaft penetrates from the outer surface to the inner surface of the proximal shaft through the penetrating portion to be exposed at the inner surface of the proximal shaft.

3. The catheter according to claim 1, wherein the tip portion of the projecting portion possesses an enlarged portion having a width larger than a width of the penetrating portion.

4. The catheter according to claim 1, wherein the penetrating portion is a hole or a slit formed to penetrate through the outer and inner surfaces of the proximal shaft.

5. The catheter according to claim 1, wherein the proximal shaft is a metallic material, and the distal shaft is a resin material.

6. The catheter according to claim 1, further comprising:
a balloon on the outer surface of the distal shaft, the balloon being distal to the projecting portion.

7. The catheter according to claim 1, further comprising:
a reinforcement body extending distally from the distal end of the proximal shaft, the reinforcement body possessing a proximal-most end,
a plurality of penetrating portions are provided in the distal end of the proximal shaft, at least one of the plurality of penetrating portions being located distal-most in the axial direction, and
the proximal-most end of the reinforcement body is distal to the at least one penetrating portion of the proximal shaft that is distal-most.

8. A catheter comprising:
a catheter shaft extending in an axial direction from a proximal end to a distal end;
the catheter shaft comprising a proximal shaft and a distal shaft; the proximal and distal shafts each being a hollow cylinder; the proximal shaft possessing a distal end, a proximal end, an inner surface and an outer surface, the distal shaft possessing a proximal end, a distal end, an inner surface and an outer surface;
the proximal end of the distal shaft being proximal to the distal end of the proximal shaft so that the distal and proximal shafts overlap in the axial direction along a joint;
the proximal shaft and the distal shaft being integrally connected to one another at the joint by the distal end of the proximal shaft being inserted into a hollow interior of the proximal end of the distal shaft;
the proximal shaft comprising a penetrating portion which penetrates from the inner surface through to the outer surface at the distal end of the proximal shaft;
the distal shaft comprising a projecting portion that extends radially inward from the inner surface of the distal shaft, the projecting portion extending through the penetrating portion of the proximal shaft to the inner surface of the proximal shaft; and
the projecting portion comprising a tip portion which extends radially inwardly beyond the inner surface of the proximal shaft.

9. The catheter according to claim 8, wherein
the penetrating portion is a hole that possesses an inner diameter,
the tip portion of the projecting portion possesses an enlarged portion possessing a width, and
the width of the enlarged portion is larger than the inner diameter of the penetrating portion.

10. The catheter according to claim 8, wherein the penetrating portion is a helical slit formed to penetrate through the outer and inner surfaces of the proximal shaft.

11. The catheter according to claim 8, wherein the proximal shaft is a metallic material and the distal shaft is a resin material.

12. The catheter according to claim 8, further comprising:
a balloon on the outer surface of the distal shaft, the balloon being distal to the projecting portion.

13. The catheter according to claim 8, further comprising:
a reinforcement body extending distally from the distal end of the proximal shaft, the reinforcement body being a wire member that possesses a proximal-most end,
a plurality of penetrating portions are provided in the distal end of the proximal shaft, at least one of the plurality of penetrating portions being distal-most in the axial direction, and
the proximal-most end of the reinforcement body is distal to the distal-most penetrating portion of the proximal shaft.

* * * * *